US006457359B1

(12) United States Patent
Suzuki

(10) Patent No.: US 6,457,359 B1
(45) Date of Patent: Oct. 1, 2002

(54) APPARATUS AND METHODS FOR MEASURING STRESS IN A SPECIMEN INCLUDING A THIN MEMBRANE

(75) Inventor: Yoshihiko Suzuki, Funabashi (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 09/656,974

(22) Filed: Sep. 7, 2000

(30) Foreign Application Priority Data

Sep. 10, 1999 (JP) ............................................. 11-256563

(51) Int. Cl.[7] .............................. G01N 29/00; G01L 1/24
(52) U.S. Cl. .............................. 73/579; 73/602; 73/800; 356/35.5
(58) Field of Search .......................... 73/579, 600, 607, 73/618, 597, 760, 800, 762, 602; 356/35.5, 432, 32, 35

(56) References Cited

U.S. PATENT DOCUMENTS

| 3,903,734 A | * | 9/1975 | Douglas ........................ 73/579 |
| 4,678,905 A | * | 7/1987 | Phillips et al. ................. 73/705 |
| 5,033,304 A | * | 7/1991 | Rosen ............................ 73/597 |
| 5,248,889 A | * | 9/1993 | Blech et al. .................. 250/561 |
| 5,546,811 A | * | 8/1996 | Rogers et al. ................. 73/800 |
| 5,748,318 A | * | 5/1998 | Maris et al. .................. 356/630 |
| 5,864,393 A | | 1/1999 | Maris ............................ 356/28 |
| 5,912,095 A | | 6/1999 | Katakura ........................ 430/5 |
| 5,959,735 A | * | 9/1999 | Maris et al. .................. 356/632 |
| 6,175,416 B1 | * | 1/2001 | Maris et al. .................. 356/630 |
| 6,208,421 B1 | * | 3/2001 | Maris et al. .................. 356/432 |

FOREIGN PATENT DOCUMENTS

JP 10-106943 4/1998

OTHER PUBLICATIONS

Anderer et al., "Determination of the Average Stress and its Adjustment in Thin Silicon Membranes Used in Various Lithographies," *Microelectronic Eng.* 5:67–71 (1986).

* cited by examiner

*Primary Examiner*—Hezron Williams
*Assistant Examiner*—Jacques Saint-Surin
(74) *Attorney, Agent, or Firm*—Klarquist Sparkman LLP

(57) ABSTRACT

Apparatus and methods are provided for measuring stresses in specimens (e.g., reticles and reticle blanks used in charged-particle-beam microlithography) that include a membrane. The disclosed apparatus and methods provide such measurements at a higher throughput than obtainable using conventional apparatus and methods. A representative stress-measuring apparatus includes a vibration-applying device that remotely (over a distance) applies a desired vibration to the membrane of the specimen. Meanwhile, a laser light source irradiates the vibrating membrane with laser light. A light receiver receives light reflected from the membrane. Electrical signals from the light receiver are processed to convert the output from the light receiver into a respective vibration spectrum. The vibration spectrum is analyzed against standard data to ascertain a strength characteristic of the membrane.

10 Claims, 3 Drawing Sheets

APPARATUS AND METHODS FOR MEASURING STRESS IN A SPECIMEN INCLUDING A THIN MEMBRANE

FIELD OF THE INVENTION

The present invention relates to apparatus and methods for measuring stress in thin films (membranes) in specimens, particularly specimens such as reticles and reticle blanks as used in charged-particle-beam microlithography apparatus and methods.

BACKGROUND OF THE INVENTION

In recent years, as individual circuit elements in semiconductor integrated circuits have become increasingly miniaturized, microlithographic exposure systems and methods offering prospects of finer resolution than obtainable by optical microlithography (which is encumbered by the diffraction limit of light) have received great R&D attention. For example, microlithographic technologies utilizing a charged particle beam (e.g., ion beam or electron beam) or X-ray beam are currently under intensive development.

One conventional microlithographic system utilizes a single electron beam to "draw" the pattern on a substrate (e.g., semiconductor wafer) line-by-line. With such technology, a fine pattern having a linewidth of 1μm or less can be produced since the electron beam can be constricted to a diameter of a few Ångstroms. Unfortunately, progressive miniaturization of a circuit typically results in a more condensed circuit with a correspondingly greater number of lines. Because these systems "draw" the pattern line-by-line, a more condensed circuit has more lines and requires a more constricted beam. Consequently, drawing time is increased, and "throughput" (number of circuits or wafers that can be processed per unit time) is correspondingly decreased. Low throughput is a key factor in making this technique unsuitable for mass-production of integrated circuits.

Another approach receiving substantial current attention is charged-particle-beam (CPB) projection microlithography in which a pattern defined on a reticle or mask is illuminated and projected ("transferred"), using the charged particle beam, to the substrate. Referring to FIG. 3(a), one type of reticle used with CPB projection microlithography is a scattering-membrane reticle 21 comprising a membrane 22 on which a pattern of scattering bodies 24 is formed. The scattering bodies 24 scatter particles of an incident charged particle beam, while the membrane 22 is relatively transmissive to such particles without scattering the beam. Referring to FIG. 3(b), another type of reticle used with CPB projection microlithography is a scattering-stencil reticle 31 comprising a membrane 32 defining a pattern of voids (through-holes). The membrane 32 has a thickness sufficient to scatter particles of an incident charged particle beam, whereas the particles pass freely through the voids.

In each of the reticles shown in FIGS. 3(a)–3(b), the pattern is divided into multiple small regions 22a, 32a each defining a respective portion of the overall pattern defined by the respective reticle. The small regions 22a, 32a are separated from each other by respective boundary regions 25, 35 that define no portion of the pattern. The boundary regions typically include struts 23, 33 extending therefrom. The struts add substantial rigidity and mechanical strength to the reticle.

Conventionally, reticles such as those shown in FIGS. 3(a)–3(b) are fabricated from "reticle blanks," which are essentially reticles lacking any pattern. Reticle blanks used for making scattering-stencil masks can be manufactured using, for example, a manufacturing process described in Japanese Kôkai Patent Publication No. Hei 10-106943. In this process, fabrication of a reticle blank begins with formation of an SOI (silicon-on-insulator) substrate. The SOI substrate is prepared from a supporting silicon substrate, a silicon oxide layer on the silicon substrate, and a silicon "active" (doped) layer on the silicon oxide layer. The silicon substrate is etched to form the struts, with regions of membrane extending between the struts. In forming the SOI substrate, the silicon oxide layer is formed by thermal oxidation of the respective surface of the silicon substrate. This oxidation step, and a subsequent step in which the silicon active layer is fused thermally with the silicon oxide layer, involve heating to respective temperatures greater than 1000 degrees. Unfortunately, due to differences in the thermal-expansion coefficients of silicon oxide versus the silicon substrate, residual thermal compressive and tensile stresses are generated in the silicon active layer as the reticle blank returns to a normal temperature. These residual stresses cause deformation of the membrane. If the residual stresses are excessively large, then substantial deformation of the pattern can arise when the reticle blank is made into a reticle.

Accordingly, to form a reticle in which the pattern formed on the reticle membrane has an optimal level of internal stress, it is highly desirable to measure and evaluate the residual internal stress of the membrane. An important known technique for obtaining such measurements and evaluations of residual membrane stress is discussed in Anderer and Behringer, "Determination of the Average Stress and Its Adjustment in Thin Silicon Membranes Used in Various Lithographies," *Microelectronic Engineering* 5:67–71,1986.

A conventional stress-measuring apparatus is shown in FIG. 4. The FIG. 4 apparatus includes a stage 42 on which the specimen (i.e., reticle or reticle blank) is mounted, a vibration-applying electrode 43 used to apply a vibration to a membrane 41a of the specimen 41, and a detection electrode 44 situated on the opposite side of the specimen 41 from the electrode 43. An AC voltage (at a desired selectable frequency) is supplied to the electrode 43 to cause the electrode 43 to generate an AC electrical field. The vibration-applying electrode 43 and detection electrode 44 normally are situated in extremely close proximity to respective surfaces of the membrane 41a. The AC electrical field electrostatically extends from the electrode 43 to the membrane 41a. Hence, the vibration-applying electrode 43 applies a vibration (corresponding to the frequency of the AC electrical field) electrostatically to the membrane 41a. As the membrane 41a is being energized in this manner, a resonance frequency of vibration of the membrane 41a is detected as corresponding changes in capacitance between the membrane 41a and the detection electrode 44.

A stress-frequency table is prepared for respective calibration membranes as determined by finite-element analysis from data concerning the length, thickness, density, Poisson ratio, and Young's modulus values of calibration membranes. The table is stored in a memory. A stress value corresponding to a particular measured resonance frequency is determined from the data in the table.

As noted above, the vibration-applying electrode 43 must be situated in extremely close proximity to the membrane 41a of the specimen 41, i.e., at a distance of 300 μm or less. The detection electrode 44 also must be placed in similar close proximity to the membrane 41a of the specimen 41.

Unfortunately, because accurate placements of the electrodes 43, 44 relative to the membrane 41a require significant time to perform, measurement throughput is low.

Furthermore, because the conventional stress-measuring device summarized above utilizes a vibration-applying electrode 43 and detection electrode 44, the device only can be used to measure stress in a conductive membrane.

SUMMARY OF THE INVENTION

In view of the shortcomings of the prior art as summarized above, an object of the invention is to provide stress-measurement apparatus and methods exhibiting improved measurement throughput. Another object is to provide such apparatus and methods that can be used to measure stress in any desired membrane, including non-conductive membranes.

According to a first aspect of the invention, apparatus are provided for measuring stress in a membrane of a specimen. A representative embodiment of such an apparatus comprises a vibration-applying device situated and configured to apply a vibration stimulus to the membrane from a distance (desirably in space from the vibration-applying device to the membrane), for example, 1.5 mm or greater. The vibration stimulus causes the membrane to experience a vibrational stress. The apparatus also comprises a detector situated and configured to measure the stress.

Desirably, the detector comprises a light source situated and configured to irradiate a region of the membrane with light such that at least a portion of the light is reflected from the membrane. The detector desirably also comprises a light receiver situated and configured to receive the light reflected from the irradiated region of the membrane and produce a corresponding output signal. Further desirably, the light receiver is connected to a computer configured to determine, from the output signal, a vibration spectrum for the irradiated region and to determine, from the vibration spectrum, a measure of a stress characteristic of the region of the membrane.

The apparatus can further comprise a signal processor connecting the light receiver to the computer. The signal processor is configured to receive the output signal from the light receiver and to convert the output signal to a corresponding digital signal routed to the computer.

The vibration-applying device desirably is configured as a piezo-electric element, and the light source desirably is a laser.

According to another aspect of the invention, methods are provided for measuring stress in a membrane of a specimen. In a representative embodiment of such a method, a vibration stimulus is directed from a source over a distance to a region of the membrane. The vibration stimulus causes the region of the membrane to vibrate. As the region of the membrane is being caused to vibrate, the region is irradiated with a light so as to produce light reflected from the region of the membrane. The reflected light is received and detected to produce a corresponding detection signal. The detection signal is converted into a corresponding vibration spectrum indicating variations in membrane-vibration amplitude with respect to vibration frequency. From the vibration spectrum, at least one resonance frequency of the membrane is determined. From the resonance frequency, a value of stress of the membrane is determined. The determination of stress desirably is performed by comparing data concerning the resonance frequency with a table of data concerning stress versus frequency for one or more membranes. The table can be stored in a memory and recalled for performing this determination. The table can be prepared by performing a finite-element analysis from data on length, thickness, density, Poisson ratio, and Young's modulus of various membranes.

The foregoing and additional features and advantages of the invention will be more readily apparent from the following detailed description, which proceeds with reference to the accompanying drawings.

DETAILED DESCRIPTION

In the following, respective representative embodiments are described of a stress-measuring device and stress-measurement method according to the invention. It will be understood that these disclosed embodiments are not to be regarded as limiting in any way.

Figure 1:
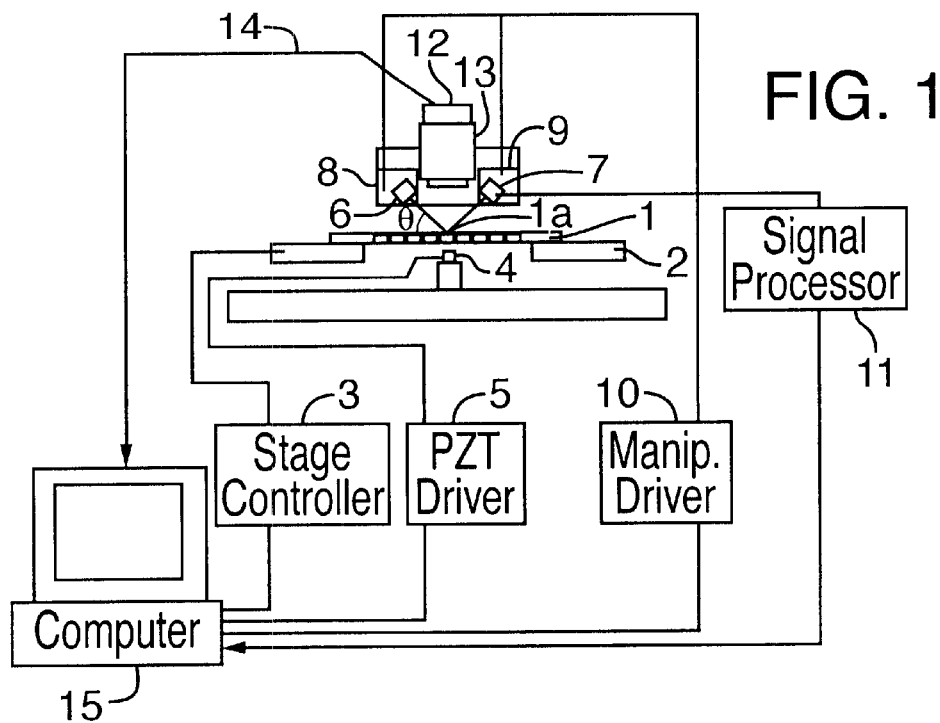
FIG. 1 is a schematic diagram of a representative embodiment of a stress-measuring apparatus according to the invention.
Figure 3A:
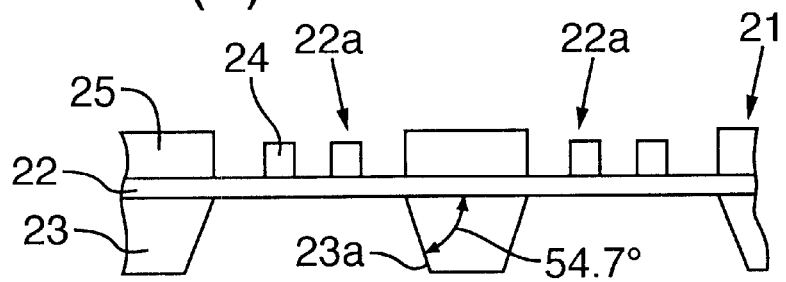
FIG. 3(a) is a schematic elevational section of a portion of a conventional divided scattering-membrane reticle used in a charged-particle-beam (CPB) microlithography apparatus.
Figure 3B:
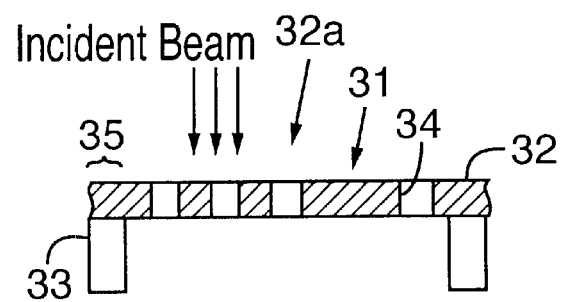
FIG. 3(b) is a schematic elevational section of a portion of a conventional divided scattering-stencil reticle used in a CPB microlithography apparatus.

A representative embodiment of a stress-measuring device according to the invention is shown in FIG. 1. The FIG. 1 embodiment includes a stage 2 configured to hold a specimen 1 (e.g., reticle or reticle blank comprising a membrane) for measurement. The stage 2 is connected to a stage controller 3, which controls movements of the stage 2 and positioning of the specimen 1 relative to a piezo-electric element 4. The piezo-electric element 4 is configured to apply a vibration over a distance to the membrane of the specimen 1. To such end, the piezo-electric element 4 is connected to a PZT controller 5 that supplies appropriate energy to the piezo-electric element 4. A laser light source 6 is mounted to a respective manipulator 8, and a multi-channel photodetector 7 is mounted to a respective manipulator 9. The photodetector 7 receives light, produced by the laser light source 6, that reflects from the surface of the specimen 1. The manipulators 8, 9 are connected to a manipulator driver 10, and the photodetector 7 is connected to a signal processor 11 that converts electrical signals from the photodetector 7 to corresponding digital signals. A specimen-observation unit 13 includes an optical system (not detailed) and a CCD (charge-coupled device) 12 that is connected to a computer 15. The optical system serves to form an image on the CCD 12. The computer 15, which controls overall operation of the FIG. 1 apparatus, also is connected to the signal processor 11, the manipulator driver 10, the PZT controller 5, and the stage controller 3. The FIG. 1 embodiment desirably also includes a first cassette (not shown) configured to hold multiple specimens (e.g., reticles or reticle blanks) awaiting measurement, and a second cassette configured to hold multiple specimens that have been measured.

A desired vibration is imparted to the membrane 1a of the specimen 1 by sound waves generated by and propagating from the piezo-electric element 4. The distance over which sound waves from the piezo-electric element 4 propagate to the specimen 1 is, by way of example, 1.5 mm or greater. The resulting vibrations of the membrane 1 a are detected using a so-called "optical lever" technique. In this technique, the angle of incidence θ (relative to the membrane 1a) of the laser light on the membrane 1a is set as desired. The magnitude of variation in laser light reflected from the membrane 1a in response to vibration (amplitude variation) applied to the membrane 1a increases as the angle of incidence θ (relative to the membrane) decreases. Desirably, the angle of incidence (relative to the membrane 1a) is in the range of 10° to 25°.

Figure 2:
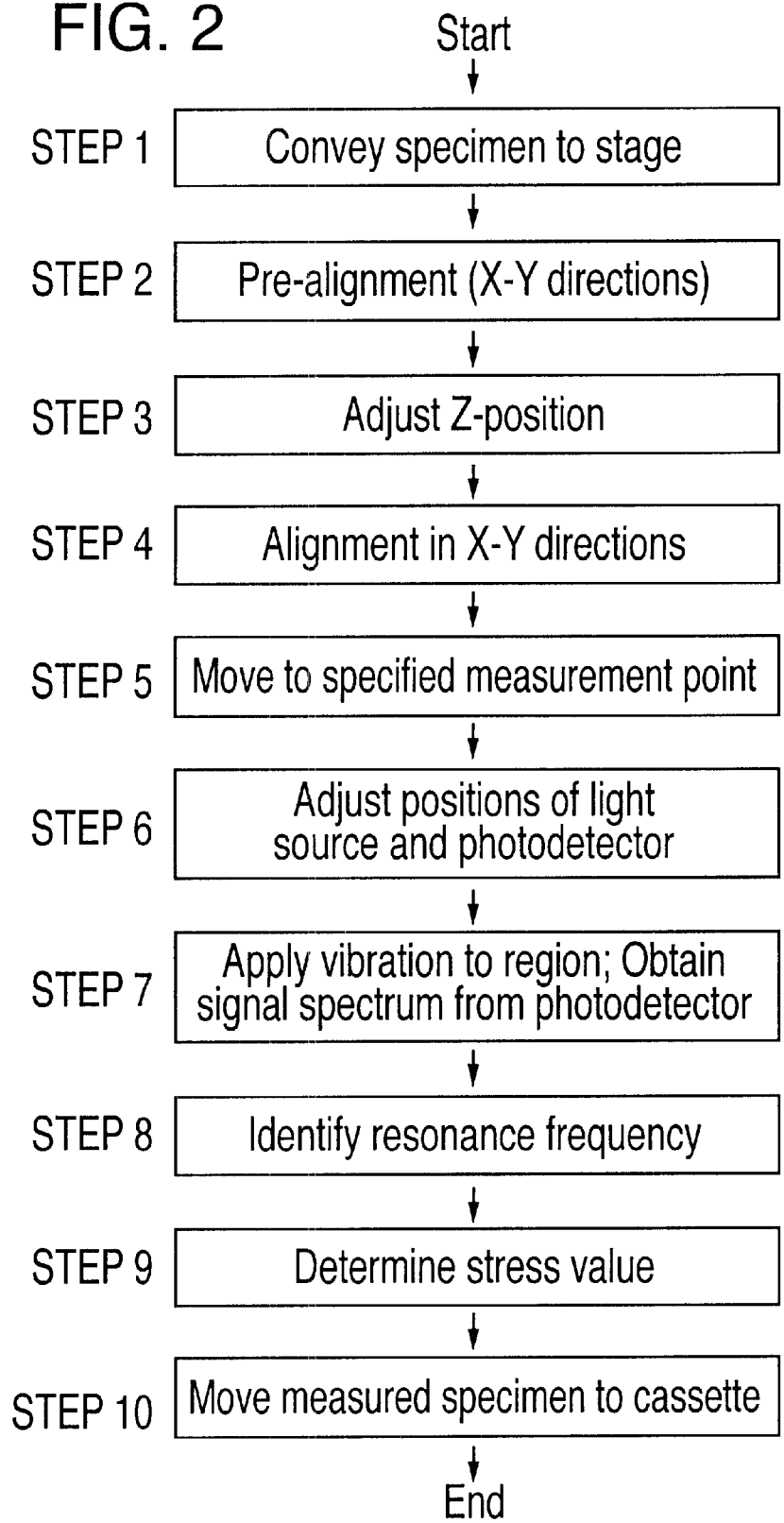
FIG. 2 is a block diagram of a representative stress-measurement method according to the invention.
Figure 4:
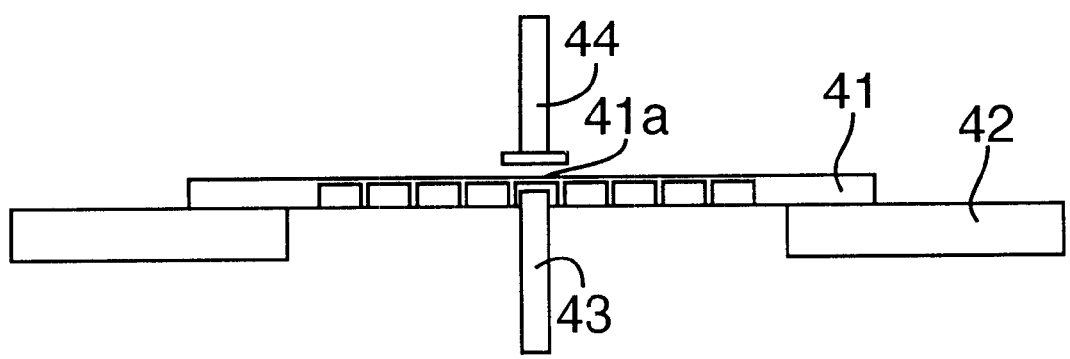
FIG. 4 is a schematic elevational view of a conventional stress-measuring device.

A representative embodiment of a stress-measurement method according to the invention is depicted in FIG. 2. The FIG. 2 method can be performed using the apparatus of FIG. 1.

In a first step (STEP 1), a specimen 1 (e.g., a reticle or reticle blank) is removed, desirably using a robotic loader (not shown), from the first cassette. The robotic loader then conveys the specimen 1 to the stage 2 and places the specimen 1 on the stage 2. Although the robotic loader and cassettes are not shown in FIG. 1, these types of devices are well known, widespread, and understood in the semiconductor-processing industry.

In STEP 2, the specimen 1 on the stage 2 is positioned. Specifically, the position of the specimen 1 in the X–Y direction is detected using a reference mark on or in the specimen 1. For example, the reference mark can be configured as a pattern of notches or orifices defined on the surface of the specimen 1. Using the reference mark, a "coarse" positioning of the specimen 1 is performed by moving the stage 2 as actuated by the stage driver 3.

In STEP 3, the membrane 1a of the specimen 1 is observed using the specimen-observation unit 13. An image of the specimen 1 is picked up by the CCD 12. On the basis of the image, the position of the specimen 1 in the Z-direction is adjusted.

In STEP 4, the position of the specimen 1 in the X–Y direction is detected using an alignment mark formed on the specimen 1 as a reference. Highly accurate positioning is accomplished by moving the stage 2 as required using the stage driver 3.

In STEP 5, the stage 2 is moved, as controlled by the stage driver 3, to position the membrane 1a of the specimen 1 at a desired specified location. Placement of the membrane 1a at the location can be monitored using the specimen-observation unit 13 (with CCD 12).

In STEP 6, a specified locus on the membrane 1a is irradiated with laser light from the laser light source 6. Laser light reflected from the membrane 1a is directed onto the center of the multi-channel photodetector 7. To ensure accurate placement of the reflected light on the photodetector 7, the position of the photodetector 7 is adjustable as required using the manipulator 9 as actuated using the driver 10. Adjustment is made until the outputs from the various channels of the photodetector 7 are equal. As the specified locus on the membrane 1 a is irradiated with laser light, the piezo-electric element 4 is energized with an AC voltage from the PZT driver 5 to produce sound waves that are directed to the specified locus. The frequency of sound waves thus directed at the locus is varied at fixed intervals within a specified frequency range, thereby causing the membrane 1a to vibrate.

In STEP 7, the angle at which the laser light is reflected from the locus varies according to the vibration amplitude of the membrane 1a. Light reflected from different locations on the vibrating membrane 1a propagates to different channels of the photodetector 7. As a result, the various channels of the photodetector 7 receive different amounts of light, and thus produce correspondingly different outputs. The outputs collectively are converted into a corresponding vibration spectrum by the signal processor 11, and the corresponding data are routed to the computer 15 for storage and analysis.

In STEP 8, the computer 15 calculates one or more resonance frequencies of the membrane 1a from the received data concerning the vibration spectrum. Using a stress-frequency table for respective membranes calculated and stored in a memory in the computer 15 (the table being calculated using, e.g., a finite-element analysis from data on the length, thickness, density, Poisson ratio, and Young's modulus values of various membranes), the computer 15 calculates a value of stress corresponding to the resonance frequency (STEP 9).

Next, the stage 2 is moved by appropriate actuation of the stage driver 3 to position the specimen 1 at the next measurement position (STEP 5). Then, STEPS 6–9 are repeated as described above.

After measurements at all desired measurement loci on the specimen 1 have been completed as described above, the specimen 1 is removed from the stage 2 and conveyed to the second cassette using a robotic loader (not shown). The second cassette holds specimens 1 with which measurements have been completed (STEP 10).

Next, STEP 1 is repeated, in which a new specimen 1 is removed from the first cassette and conveyed to the stage 2 using a robotic loader. Afterward, STEPS 2–9 are repeated for the new specimen 1, as described above.

The specimen 1 typically is a reticle blank. As discussed above, the reticle blank normally is divided into multiple small areas (e.g., "subfields") by boundary regions that define no respective pattern portions in the finished reticle. The boundary regions typically are where supporting struts are located. Whenever such a specimen is exposed to localized sound waves having a frequency of 1 to 200 KHz, vibrations at certain resonance frequencies are generated in the small areas, but almost no vibration occurs in the boundary regions. In other words, in instances in which such a specimen receives a sonic stimulus, significant differences are evident, at certain resonance frequencies, between the boundary regions and small areas consisting of the membrane.

It is possible to increase the surface area of the piezo-electric element 4 so that sound waves are propagated from multiple small areas at any one instance. To such end, a device (such as a beamsplitter) can be used to split the irradiating laser light from the laser light source 6 into a corresponding plurality of laser beams. Multiple detectors 7 can be used simultaneously to receive reflected light from the multiple small areas. Thus, stress can be measured simultaneously from multiple small areas.

As an alternative to using a piezo-electric element to apply the vibration to the membrane 1a, it is possible to use a mechanical mechanism capable of applying the vibration from a distance. Known methods for applying vibration using a mechanical mechanism include situating a piezo-electric element in a member contacted by the specimen 1 on the stage 2, so that the vibration is applied directly in a mechanical manner to the specimen.

As an alternative to the multi-channel photodetector 7, a one-dimensional CCD or two-dimensional CCD, for example, can be used to receive reflected light from the specimen 1.

As noted above, any of various specimens can be measured. Representative specimens include reticles, reticle blanks, and piezo-electric sensor elements.

Because vibration is applied to the specimen over a substantially greater distance than conventionally, proper positioning of the specimen can be accomplished in a very short time. This allows corresponding increases in measurement throughput.

Whereas the invention has been described in connection with representative embodiments, it will be understood that the invention is not limited to those embodiments. On the contrary, the invention is intended to encompass all modifications, alternatives, and equivalents as may be included within the spirit and scope of the invention, as defined by the appended claims.

What is claimed is:

1. An apparatus for measuring stress in a membrane of a specimen, the apparatus comprising:

a vibration-applying device situated a distance from the membrane and configured to apply a vibration stimulus comprising sound waves to the membrane, the vibration stimulus causing the membrane to experience a vibrational stress; and a detector situated and configured to measure the stress, the detector comprising a light source situated and configured to irradiate a region of the membrane with light such that at least a portion of the light is reflected from the membrane, a light receiver situated and configured to receive the light reflected from the irradiated region of the membrane and produce a corresponding output signal, and a computer connected to the light receiver and configured to determine, from the output signal, a vibration spectrum for the irradiated region and to determine, from the vibration spectrum, a measure of a stress characteristic of the region of the membrane.

2. The apparatus of claim 1, further comprising a signal processor connecting the light receiver to the computer, the signal processor being configured to receive the output signal from the light receiver and to convert the output signal to a corresponding digital signal routed to the computer.

3. The apparatus of claim 1, wherein the light source is a laser.

4. The apparatus of claim 1, wherein the vibration-applying device is configured as a piezo-electric element.

5. The apparatus of claim 1, wherein the distance is in space from the vibration-applying device to the membrane.

6. The apparatus of claim 1, wherein the distance is 1.5 mm or greater.

7. A method for measuring stress in a membrane of a specimen, the method comprising the steps:

(a) directing a vibration stimulus comprising sound waves from a source over a distance to a region of the membrane, the vibration stimulus causing the region of the membrane to vibrate;

(b) as the region of the membrane is being caused to vibrate, irradiating the region with a light so as to produce light reflected from the region of the membrane;

(c) receiving and detecting the reflected light to produce a corresponding detection signal;

(d) converting the detection signal into a corresponding vibration spectrum indicating variations in membrane-vibration amplitude with respect to vibration frequency;

(e) from the vibration spectrum, determining at least one resonance frequency of the membrane; and (f) from the resonance frequency, calculating a value of stress of the membrane.

8. The method of claim 7, wherein step (f) is performed by comparing data concerning the resonance frequency with a table of data concerning stress versus frequency for one or more membranes.

9. The method of claim 8, wherein the table is stored in a memory and recalled for performing step (f).

10. The method of claim 8, wherein the table is obtained by performing a finite-element analysis from data on length, thickness, density, Poisson ratio, and Young's modulus of various membranes.

* * * * *

UNITED STATES PATENT AND TRADEMARK OFFICE
CERTIFICATE OF CORRECTION

PATENT NO.     : 6,457,359 B1
DATED          : October 1, 2002
INVENTOR(S)    : Suzuki It is certified that error appears in the above-identified patent and that said Letters Patent is hereby corrected as shown below:

<u>Column 5,</u>
Line 4, "1 a" should be -- 1a --.
Line 59, "1 a" should be -- 1a --.

Signed and Sealed this

Twenty-first Day of October, 2003

JAMES E. ROGAN
*Director of the United States Patent and Trademark Office*